United States Patent
Akram et al.

(10) Patent No.: US 6,916,343 B1
(45) Date of Patent: Jul. 12, 2005

(54) METHOD FOR COLORING HAIR

(75) Inventors: Mustafa Akram, Hamburg (DE); Rolf-Werner Haubold, Hamburg (DE)

(73) Assignee: Hans Schwarzkopf GmbH & Co. KG, Hamburg (DE)

(*) Notice: Subject to any disclaimer, the term of this patent is extended or adjusted under 35 U.S.C. 154(b) by 0 days.

(21) Appl. No.: 10/069,849

(22) PCT Filed: Aug. 22, 2000

(86) PCT No.: PCT/EP00/08175

§ 371 (c)(1), (2), (4) Date: Feb. 28, 2002

(87) PCT Pub. No.: WO01/15662

PCT Pub. Date: Mar. 8, 2001

(30) Foreign Application Priority Data

Aug. 31, 1999 (DE) .......................... 199 41 450

(51) Int. Cl.$^7$ .................................. A11K 7/13
(52) U.S. Cl. ..................... 8/405; 8/406; 8/407; 8/410; 8/411; 8/421; 8/426; 8/437; 8/454; 8/455; 8/542
(58) Field of Search ........................ 8/405, 406, 407, 8/410, 411, 421, 426, 437, 454, 455, 542

(56) References Cited

U.S. PATENT DOCUMENTS

| | | | |
|---|---|---|---|
| 4,425,132 A | * 1/1984 | Grollier et al. | 8/405 |
| 4,865,774 A | 9/1989 | Fabry et al. | 252/554 |
| 4,931,218 A | 6/1990 | Schenker et al. | 252/551 |
| 5,073,174 A | 12/1991 | Vayssie et al. | 8/405 |
| 5,294,726 A | 3/1994 | Behler et al. | 554/98 |
| 5,534,267 A | 7/1996 | Neunhoeffer et al. | 424/701 |
| 5,954,871 A | * 9/1999 | Nicolas-Morgantini et al. | 106/502 |
| 6,099,592 A | 8/2000 | Vidal et al. | 8/409 |
| 6,129,770 A | 10/2000 | Deutz et al. | 8/406 |
| 6,338,741 B1 | 1/2002 | Vidal et al. | 8/409 |

FOREIGN PATENT DOCUMENTS

| | | |
|---|---|---|
| DE | 37 23 354 | 1/1989 |
| DE | 37 25 030 | 2/1989 |
| DE | 39 26 344 | 2/1991 |
| DE | 195 22 569.4 | 6/1995 |
| DE | 196 17 515 | 1/1997 |
| EP | 0 740 931 | 11/1996 |
| WO | WO 90/01922 | 3/1990 |
| WO | WO 92/13829 | 8/1992 |
| WO | WO 94/08970 | 4/1994 |

OTHER PUBLICATIONS

K. Schrader, Grundlagen un Rezepturen der Kosmetika [Bases and Formulations in Cosmetics], $2^{nd}$ Edition, pp. 782–799, Huethig Buch Verlag, Heidelberg, Germany (1989).

The Science of Hair Care, Chapter 7, pp. 235–261, published in vol. 7 of Dermatology, Marcel Dekker Inc. NY/Basle (1986).

The Science of Hair Care, Chapter 8, pp. 263–286, published in vol. 7 of Dermatology, Marcel Dekker Inc. NY/Basle (1986).

EU Inventory of Cosmetic Ingredients, Colipa, Mar. 1996 on diskette.

"Leitfaden zur Inhaltsstoffdeklaration kosmetischer Mittel," herausgegeben vom Industrieverband Körperpfleg und Waschmittel e.V. (IKW), $3^{rd}$ Edition, pp. 44–62, Frankfurt 1995.

* cited by examiner

*Primary Examiner*—Margaret Einsmann
*Assistant Examiner*—Eisa Elhilo
(74) *Attorney, Agent, or Firm*—Stephen D. Harper

(57) ABSTRACT

A method for coloring keratin fibers is provided that includes at least two steps. In one step, the keratin fibers are treated with a pretreatment composition containing at least one substantive dye. In another step, the keratin fibers are treated with a composition containing at least one synthetic dye or synthetic dye precursor after applying the pretreatment composition.

18 Claims, No Drawings

METHOD FOR COLORING HAIR

CROSS REFERENCE TO RELATED APPLICATIONS

This application is a national stage application under 35 U.S.C. § 371 of international application PCT/EP00/08175 filed on Aug. 22, 2000, the international application not being published in English. This application also claims priority under 35 U.S.C. §119 to DE 199 41 450.5 filed on Aug. 31, 1999.

BACKGROUND OF THE INVENTION

This invention relates to a two-stage process for coloring keratin fibers and to the use of a special pretreatment composition in this process.

Preparations for tinting and coloring hair are an important type of cosmetic product. They may be used to give the natural color of the hair a light or relatively dark shade, to obtain a totally different hair color or to cover unwanted color tones, for example gray tones, according to the wishes of the particular user. Conventional hair colorants are formulated either on the basis of oxidation dyes or on the basis of substantive dyes according to the required color or the permanence thereof. In many cases, combinations of oxidation dyes and substantive dyes are also used to obtain special shades.

Colorants based on oxidation dyes lead to brilliant and permanent color tones. However, they do involve the use of strong oxidizing agents, such as hydrogen peroxide solutions for example. Colorants such as these contain oxidation dye precursors, so-called primary intermediates and secondary intermediates. The primary intermediates form the actual dyes with one another or by coupling with one or more secondary intermediates under the influence of oxidizing agents or atmospheric oxygen.

Colorants based on substantive dyes do not require oxidizing agents and may be formulated at pH values near the neutral point. A major disadvantage of colorants based on substantive dyes is the poor fastness to washing of the colors obtained. In many cases, the capacity of the dye molecules for absorption onto the hair and the shine of the colored hair are not entirely satisfactory either.

Nevertheless, these known coloring methods are still not totally convincing. In many cases, an uneven color impression is created after coloring, particularly with the so-called fashionable shades in the red, copper and gold range, the hair fibers showing a loss of brilliance at their tips. This unevenness of coloring is attributable to the different care states of the hair fibers in the freshly regrown parts and the tips which may have become more porous through previous treatments or environmental influences. Accordingly, the problem addressed by the present invention was to provide a coloring process for keratin fibers which would not have the disadvantages mentioned above and which would lead to colors with excellent fastness properties.

It has now surprisingly been found that highly uniform colors with excellent fastness properties—even in the case of fashionable red, copper and gold shades—can be obtained if the fibers are treated in a first step with a pretreatment composition containing substantive dyes and are subjected in a second step to conventional coloring with at least one synthetic dye (precursor).

Two-stage processes for coloring keratin fibers have been known for some time. WO 90/01922-A1, for example, discloses a hair coloring process in which the hair is treated in a first step with a preparation containing a substantive dye and in a second step with a preparation containing natural dyes. However, there is nothing in that document which points to the advantages of the process according to the present invention. In many cases, such coloring processes were very complex and could only be carried out by professionals. In addition, the colors obtained with such processes were still not entirely satisfactory in regard to evenness and fastness.

SUMMARY OF THE INVENTION

In a first embodiment, therefore, the present invention relates to a two-stage process for coloring keratin fibers in which the fibers are treated in a first step with a pretreatment composition containing at least one substantive dye and in a second step with a conventional colorant containing at least one synthetic dye (precursor).

DETAILED DESCRIPTION OF THE INVENTION

Keratin fibers in the context of the present invention are understood to include pelts, wool, feathers and, in particular, human hair.

Substantive dyes are typically nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, HC Yellow 12, Basic Yellow 57, Acid Yellow 1 (CI 10316), Disperse Orange 3, HC Red 3, HC Red BN, Basic Red 2, Basic Red 76, Acid Red 87 (CI 45380), HC Blue 2, HC Blue 12, Disperse Blue 3, Basic Blue 7, Basic Blue 99, FD&C Green (CI 42053), D&C Green No. 8 (CI 59040), HC Violet 1, Basic Violet 14, Disperse Violet 1, Disperse Violet 4, Disperse Black 9, Acid Black 52, Basic Brown 16 and Basic Brown 17 and also 1,4-bis-($\beta$-hydroxyethyl)-amino-2-nitrobenzene, 4-amino-2-nitro-diphenylamine-2'-carboxylic acid, 6-nitro-1,2,3,4-tetrahydroquinoxaline, hydroxyethyl-2-nitrotoluidine, picramic acid, sodium picramate, 2-amino-6-chloro-4-nitrophenol, 4-ethylamino-3-nitrobenzoic acid and 2-chloro-6-ethylamino-1-hydroxy-4-nitrobenzene.

Although the pretreatment composition may in principle contain any substantive dyes, nitrobenzene derivatives, basic substantive dyes and triphenyl methane derivatives have proved to be particularly suitable, particularly where coloring in the second stage is oxidative. Particularly preferred dyes for the purposes of the invention are 3-nitro-4-aminophenol, 4-(3'-hydroxypropylamino)-3-nitrophenol (HC Red BN), 1,4-bis-($\beta$-hydroxyethyl)-amino-2-nitrobenzene, 1-($\beta$-hydroxyethylamino)-2-nitro-4-aminobenzene (HC Red No. 3), 1-($\beta$-hydroxyethylamino)-2-nitrobenzene (HC Yellow No. 2), 4-($\beta$-hydroxyethylamino)-3-nitrophenol, HC Blue 2, Basic Blue 99, Basic Red 76, Basic Brown 16 and Basic Brown 17.

The pretreatment compositions according to the invention contain the substantive dyes in a quantity of preferably 0.001 to 20% by weight, more preferably 0.005 to 5% by weight and most preferably 0.01 to 1% by weight, based on the pretreatment composition as a whole.

The pretreatment composition according to the invention contains the substantive dyes in a suitable water-containing carrier. The pretreatment compositions may additionally contain other organic solvents such as, for example, methoxybutanol, benzyl alcohol, isopropyl alcohol, ethyl diglycol or 1,2-propylene glycol. Preferred solvents are any water-soluble organic solvents.

In addition, carriers according to the invention are creams, emulsions, gels or even surfactant-containing foaming solutions, for example shampoos, foam aerosols or other preparations suitable for application to the hair. Although there is nothing to prevent formulation of the pretreatment composition in any of the forms mentioned, it has proved to be of particular advantage in the interests of uniform coloring and easier handling to formulate the pretreatment composition as a spray.

In a particularly preferred embodiment, the pretreatment composition is formulated as a propellant-free pump spray. Nevertheless, it may also be formulated as a propellant-containing spray. In principle, any liquefiable gases used in the cosmetics field and air may be used as propellants. Such gases include, for example, lower alkanes, dimethylether and fluorochlorocarbons and fluorocarbons. The propellant(s) is/are preferably selected so that the preparations according to the invention form stable homogeneous mixtures even after prolonged periods under storage conditions typical of cosmetic products. Preferred propellants are lower alkanes, more particularly propane, butane, isobutane and mixtures of these alkanes.

The preparations according to the invention contain the propellants in quantities of preferably 1 to 20% by weight and more particularly 2 to 10% by weight, based on the preparation as a whole.

In a preferred embodiment of the present invention, the pretreatment composition contains a fiber-structure-improving agent besides the substantive dyes. Examples of such agents are panthenol and its physiologically compatible derivatives. Such derivatives are in particular the esters and ethers of panthenol and cationically derivatized panthenols. Individual representatives are, for example, panthenol triacetate, panthenol monomethyl ether and its monoacetate and the cationic panthenol derivatives disclosed in WO 92/13829. Within this group, panthenol is particularly preferred.

Another suitable group of fiber-structure-improving agents are plant extracts.

These extracts are normally prepared by extraction of the whole plant. In some cases, however, it may even be preferable to prepare the extracts solely from blossoms and/or leaves of the plants.

So far as the plant extracts suitable for use in accordance with the invention are concerned, particular reference is made to the extracts listed in the Table beginning on page 44 of the 3rd Edition of the Leitfaden zur Inhaltsstoffdeklaration kosmetischer Mittel, published by the Industrieverband Körperpflege- und Waschmittel e.V. (IKW), Frankfurt.

According to the invention, particular preference is attributed above all to the extracts of oak bark, stinging nettle, hamamelis, hops, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, green tea ginseng and ginger root.

Particularly preferred extracts are those of oak bark, stinging nettle, hamamelis, hops, camomile, burdock root, horse willow, lime blossom, almond, aloe vera, coconut, mango, apricot, lemon, wheat, kiwi, melon, orange, grapefruit, sage, rosemary, birch, lady's smock, creeping thyme, yarrow, restharrow, meristem, green tea ginseng and ginger root.

The extracts of almond, aloe vera, coconut, mango, apricot, lemon, wheat, kiwi, melon and green tea are most particularly preferred for the use according to the invention.

Water, alcohols and mixtures thereof may be used as extractants for preparing the plant extracts mentioned. Preferred alcohols are lower alcohols, such as ethanol and isopropanol, but especially polyhydric alcohols, such as ethylene glycol and propylene glycol, both as sole extractant and in admixture with water. Plant extracts based on water/propylene glycol in a ratio of 1:10 to 10:1 have proved to be particularly suitable.

According to the invention, the plant extracts may be used both in pure form and in dilute form. If they are used in dilute form, they normally contain ca. 2 to 80% by weight active substance and, as solvent, the extractant or extractant mixture used in their preparation.

In another preferred embodiment, mixtures of several, more particularly two, different plant extracts may be used in the compositions according to the invention.

According to the invention, honey extracts are also preferred fiber-structure-improving agents. These extracts are obtained similarly to the plant extracts and normally contain 1 to 10% by weight and more particularly 3 to 5% by weight of active substance. Water/propylene glycol mixtures can again be preferred extractants.

Other fiber-structure-improving agents are protein hydrolyzates, more particularly elastin, collagen, keratin, milk protein, soya protein, almond protein and wheat protein hydrolyzates, condensation products thereof with fatty acids and quaternized protein hydrolyzates. Fiber-structure-improving agents also include mono-, di- and oligosaccharides such as, for example, glucose, galactose, fructose and lactose.

Certain amino acids may also be used as fiber-structure-improving agents for the purposes of the present invention. Examples are the amino acids serine, threonine and tyrosine described in DE 195 22 569 to which reference is specifically made here. Serine is a particularly preferred fiber-structure-improving agent.

The pretreatment compositions according to the invention may also contain any of the known active substances, additives and auxiliaries typical of such preparations. In many cases, the pretreatment compositions contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O($CH_2$—$CH_2$O)$_x$—$SO_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment compositions according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the products marketed under the trade name of Dehyquart®—such as Dehyquart® AU-46 and Dehyquart® L-80—are also readily biodegradable. The esterquats are the particularly preferred surfactants for the purposes of the invention.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example,

- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol,
- zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers,
- anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers,
- thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as maleic acid and lactic acid,
- hair-conditioning compounds, such as phospholipids, for example soybean lecithin, egg lecithin and kephalins, and also silicone oils,
- perfume oils, dimethyl isosorbide and cyclodextrins,
- cholesterol,
- light filters,
- consistency factors, such as sugar esters, polyol esters or polyol alkyl ethers,
- fats and waxes, such as spermaceti, beeswax, montan wax, paraffins, fatty alcohols and fatty acid esters,
- fatty acid alkanolamides,
- complexing agents, such as EDTA, NTA and phosphonic acids,
- swelling and penetration agents, such as glycerol, propylene glycol monoethyl ether, carbonates, hydrogen carbonates, guanidines, ureas and primary, secondary and tertiary phosphates,
- opacifiers, such as latex,
- pearlizers, such as ethylene glycol mono- and distearate,
- antioxidants.

There are no limits to the contact time of the pretreatment composition. However, it has proved to be of advantage for the contact time to be between 1 and 30 minutes, preferably between 1 and 10 minutes and most particularly between 3 and 5 minutes. Even though, in principle, there is no need for an intermediate treatment before conventional hair coloring in the second step, it has proved to be of advantage for excess liquid to be removed after the contact time by dabbing, stripping or drying before the second hair colorant is applied.

The hair treatment compositions according to the invention are preferably formulated so that they have a pH between 3 and 9, preferably between 4 and 8 and more preferably between 4 and 5. The pH may be adjusted with any of the acids and alkalizing agents used for this purpose in the cosmetics field.

The notion of conventional coloring with at least one synthetic dye (precursor) in the second step of the process according to the invention encompasses all processes known to the expert where a colorant is applied to the hair and is either left on the hair for a few minutes to ca. 45 minutes and then rinsed out with water or a surfactant-containing shampoo or is left entirely on the hair. Reference is specifically made in this connection to the known works which reproduce the relevant knowledge of the expert, for example Kh. Schrader, Grundlagen und Rezepturen der Kosmetika, 2nd Edition, Hüthig Buch Verlag, Heidelberg, 1989.

The are no basic restrictions to the composition of the conventional colorant.

Suitable dye (precursor)s include

- oxidation dye precursors of the primary and secondary intermediate type,
- synthetic substantive dyes and
- precursors of "nature-like" dyes, such as indole and indoline derivatives and mixtures of representatives of one of more of these groups.

Oxidation dye precursors of the primary intermediate type are normally primary aromatic amines with another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof. Suitable primary intermediates are, for example, p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 4-amino-3-methylphenol, 2,4,5, 6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4, 5,6-triaminopyrimidine, 2-hydroxymethylaminomethyl-4-aminophenol, bis-(4-aminophenyl)-amine, 4-amino-3-fluorophenol, 2-aminomethyl-4-aminophenol, 2-hydroxymethyl-4-aminophenol, 4-amino-2-(diethylamino)-methyl)-phenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol, 1,10-bis-(2,5-diaminophenyl)-1,4, 7,10-tetraoxadecane and 4,5-diaminopyrazole derivatives according to EP 0 740 931 or WO 94/08970, for example 4,5-diamino-1-(2'-hydroxyethyl)-pyrazole. Particularly advantageous primary intermediates are p-phenylenediamine, p-toluylenediamine, p-aminophenol, 1-(2'-hydroxyethyl)-2,5-diaminobenzene, 4-amino-3-methylphenol, 2-aminomethyl-4-aminophenol, 2,4,5,6-tetraaminopyrimidine, 2-hydroxy4,5,6-triaminopyrimidine and 4-hydroxy-2,5,6-triaminopyrimidine.

The primary intermediates p-phenylenediamine, p-toluylenediamine, p-aminophenol, 1-(2'-hydroxyethyl)2, 5-diaminobenzene, 4-amino-3-methylphenol, 2-aminomethyl-4-aminophenol and 2,4,5,6-tetraaminopyrimidine have proved to be particularly preferred, especially for obtaining fashionable colors.

m-Phenylenediamine derivatives, naphthols, resorcinol and resorcinol derivatives, pyrazolones and m-aminophenol derivatives are generally used as oxidation dye precursors of the secondary intermediate type. Examples of such secondary intermediates are m-aminophenol and derivatives thereof such as, for example, 5-amino-2-methylphenol, 5-(3-hydroxypropylamino)-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2,4-diaminophenoxy)-propane, 1-methoxy-2-amino-4-(2'-hydroxyethylaminoy benzene, 1,3-bis-(2,4-diaminophenyl)-propane, 2,6-bis-(2-hydroxyethyl-amino)-1-methylbenzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy4-methylpyridine, 2,6-diaminopyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihdroxynaphthalene, 1,8-dihdroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, methylenedioxybenzene derivatives such as, for example, 1-hydroxy-3,4-methylenedioxybenzene, 1-amino-3,4-methylenedioxybenzene and 1-(2'-hydroxyethyl)-amino-3,4-methylenedioxybenzene.

Particularly suitable secondary intermediates are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol, 2,6-di-(β-hydroxyethylamino)toluene and 2,6-dihydroxy-3,4-dimethylpyridine.

Most particularly preferred secondary intermediates, especially for obtaining fashionable colors in the red range, are 2-chloro-6-methyl-3-aminophenol, 5-amino-2-methylphenol, 2-amino-3-hydroxypyridine, 2,6-di-(β-hydroxyethylamino)-toluene, 2-methyl resorcinol and 1-naphthol.

The primary/secondary intermediate combination of 2,4, 5,6-tetraaminopyrimidine and 2-methyl resorcinol is particularly preferred for obtaining reddish shades.

So far as the substantive dyes suitable for the purposes of the invention are concerned, reference is made at this juncture to the foregoing observations.

Besides the synthetic dye (precursor), naturally occurring substantive dyes, such as, for example, henna red, henna neutral, henna black, camomile blossom, sandalwood, black tea, black alder bark, sage, logwood, madder root, catechu, sedre and alkanet, may also be used to obtain further shades.

Neither the oxidation dye precursors nor the substantive dyes have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting compositions according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basel, 1986, and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel d.V., Mannheim.

Both the oxidation dye precursors and the substantive dyes are present in the preparations according to the invention in quantities of preferably 0.01 to 20% by weight and more preferably 0.5 to 5% by weight, based on the preparation as a whole.

Preferred precursors of natural dyes are indoles and indolines which contain at least one hydroxy or amino group, preferably as a substituent on the six-membered ring. These groups may carry further substituents, for example in the form of an etherification or esterification of the hydroxy group or an alkylation of the amino group.

Particularly suitable precursors of natural hair dyes are derivatives of 5,6-dihydroxyindoline corresponding to formula (Ia):

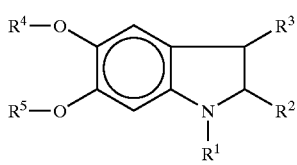

(Ia)

in which—independently of one another—$R^1$ is hydrogen, a $C_{1-4}$ alkyl group or a $C_{1-4}$ hydroxyalkyl group, $R^2$ is hydrogen or a —COOH group, the —COOH group optionally being present as a salt with a physiologically compatible cation, $R^3$ is hydrogen or a $C_{1-4}$ alkyl group, $R^4$ is hydrogen, a $C_{1-4}$ alkyl group or a group —CO—$R^6$, where $R^6$ is a $C_{1-4}$ alkyl group, and $R^5$ is one of the groups mentioned for $R^4$, and physiologically compatible salts of these compounds with an organic or inorganic acid.

Particularly preferred derivatives of indoline are 5,6-hydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Other particularly suitable precursors of natural hair dyes are derivatives of 5,6-dihydroxyindole corresponding to formula (Ib):

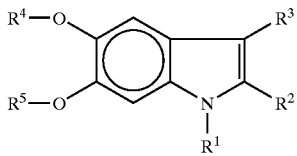

(Ib)

in which—independently of one another—

$R^1$ is hydrogen, a $C_{1-4}$ alkyl group or a $C_{1-4}$ hydroxyalkyl group, $R^2$ is hydrogen or a —COOH group, the —COOH group optionally being present as a salt with a physiologically compatible cation, $R^3$ is hydrogen or a $C_{1-4}$ alkyl group, $R^4$ is hydrogen, a $C_{1-4}$ alkyl group or a group —CO—$R^6$, where $R^6$ is a $C_{1-4}$ alkyl group, and $R^5$ is one of the groups mentioned for $R^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used both as free bases and in the form of their physiologically compatible salts with inorganic or organic acids, for example hydrochlorides, sulfates and hydrobromides, in the colorants used in the process according to the invention. The indole or indoline derivatives are present in these colorants in quantities of normally 0.05 to 10% by weight and preferably 0.2 to 5% by weight.

Where dye precursors of the indoline or indole type are used, it can be of advantage to use them together with at least one amino acid and/or at least one oligopeptide. Preferred amino acids are aminocarboxylic acids, more particularly α-aminocarboxylic acids and ω-aminocarboxylic acids. Among the α-aminocarboxylic acids, arginine, lysine, ornithine and histidine are particularly preferred. A most particularly preferred amino acid is arginine used more particularly in free form but also as the hydrochloride.

Hair colorants are normally adjusted to a mildly acidic to alkaline pH, i.e. to a pH of about 5 to 11, particularly where coloring is carried out oxidatively with atmospheric oxygen or other oxidizing agents, such as hydrogen peroxide. To this end, the colorants contain alkalizing agents, normally alkali metal or alkaline earth metal hydroxides, ammonia or organic amines. Preferred alkalizing agents are monoethanolamine, monoisopropanolamine, 2-amino-2-methylpropanol, 2-amino-2-methylpropane-1,3-diol, 2-amino-2-ethylpropane-1,3-diol, 2-amino-2-methylbutanol and triethanolamine and alkali metal and alkaline earth metal hydroxides. Within this group, monoethanolamine, triethanolamine and 2-amino-2-methylpropanol and 2-amino-2-methylpropane-1,3-diol are preferred. ω-Amino acids, such as ω-aminocaproic acid, may also be used as alkalizing agents.

If the actual hair colors are developed in an oxidative process, typical oxidizing agents such as, in particular, hydrogen peroxide or adducts thereof with urea, melamine or sodium borate may be used. However, oxidation with atmospheric oxygen as sole oxidizing agent may be preferred. Oxidation may also be carried out with enzymes. In this case, the enzymes may be used both to produce oxidizing per compounds and to enhance the effect of an oxidizing agent present in small quantities.

Thus, the enzymes (enzyme class 1: oxidoreductases) are capable of transferring electrons from suitable primary intermediates (reducing agents) to atmospheric oxygen. Preferred enzymes are oxidases, such as tyrosinase and laccase, although glucoseoxidase, uricase or pyruvate oxidase may also be used. Mention is also made of the procedure whereby the effect of small quantities (for example 1% and less, based on the composition as a whole) of hydrogen peroxide is strengthened by peroxidases.

The preparation of the oxidizing agent is preferably mixed with the preparation of the oxidation dye precursors immediately before coloring of the hair. The ready-to-use hair coloring preparation formed should have a pH value in the range from 6 to 10. In a particularly preferred embodiment, the hair colorant is used in a mildly alkaline medium. The application temperatures may be in the range from 15 to 40° C. but are preferably at the temperature of the scalp. After a contact time of about 5 to 45 and preferably 15 to 30 minutes, the hair colorant is removed from the hair to be colored by rinsing. There is no need for the hair to be washed with a shampoo where a carrier of high surfactant content, for example a coloring shampoo, has been used.

In the particular case of hair which is difficult to color, the preparation containing the oxidation dye precursors may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed. In a first variant of this embodiment where the preliminary application of the dye precursors is intended to improve penetration into the hair, the corresponding formulation is adjusted to a pH value of about 4 to 7. In a second variant, oxidation with air is initially carried out, the formulation applied preferably having a pH value of 7 to 10. In the subsequent accelerated post-oxidation phase, it can be of advantage to use acidified peroxydisulfate solutions as the oxidizing agent.

Whichever of the processes mentioned above is used to apply the colorant according to the invention, development of the color may be supported and enhanced by adding certain metal ions to the colorant. Examples of such metal ions are $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. Basically, the metal ions may be used in the form of a physiologically compatible salt. Preferred salts are the acetates, sulfates, halides, lactates and tartrates. Development of the hair color can be accelerated and the color tone can be influenced as required through the use of these metal salts.

The present invention also relates to the use of a pretreatment composition containing at least one substantive dye in a hair coloring process for obtaining a uniform color.

In one preferred embodiment of this use, the pretreatment composition is formulated as a spray. For further formulations, see the foregoing observations.

The following Examples are intended to illustrate the invention.

EXAMPLES

In the following Examples, all quantities are parts by weight unless otherwise stated.

Example 1

In a volunteer with dark blond hair with very porous tips, the hair was divided by a center parting into a left-hand half and a right-hand half.

The left-hand half was treated as follows:

The porous hair tips were sprayed with ca. 15 g of formulation A1. After a contact time of 8 minutes at 25° C., the hair was treated over its entire length with a mixture of 30 g of formulation B1 and 30 g of a 6% aqueous hydrogen peroxide solution. After a contact time of 30 minutes at 25° C., the hair was rinsed with water, shampooed and blow-dried.

The right-hand half was treated as follows:

The hair was treated over its entire length with a mixture of 30 g of formulation B1 and 30 g of a 6% aqueous hydrogen peroxide solution. After a contact time of 30 minutes at 25° C., the hair was rinsed with water, shampooed and blow-dried.

Result:

The left-hand side was uniformly and intensively red in color from the roots to the tips. The right-hand side was less uniformly and less intensively red-colored.

Permanence Test:

The hair was washed daily on both sides for 12 days with a commercially available shampoo. The result showed that color removal is greater on the right-hand side than on the left-hand side.

| Formulation A1 | | |
|---|---|---|
| Natrosol ® 250 HR[1] | | 0.2 |
| Dehyquart ® L-80[2] | | 0.3 |
| panthenol | | 0.1 |
| p-hydroxybenzoic acid methyl ester | | 0.03 |
| p-hydroxybenzoic acid propyl ester | | 0.03 |
| methoxybutanol | | 2.0 |
| 4-hydroxypropylamino-3-nitrophenol | | 0.2 |
| Basic Red 76 | | 0.2 |
| water | to | 100 |
| Formulation B1 | | |
| ammonium carbopol solution, 1% in water[3] | | 17.25 |
| ammonium rohagit solution, 6% in water[4] | | 5.25 |
| Oleth-7[5] | | 5.70 |
| potassium olein soap, 12.5% in water | | 3.45 |
| Plantaren ® 2000[6] | | 0.53 |
| titanium dioxide anatase, type AS 05 | | 0.48 |
| Cetiol ® V[7] | | 3.45 |
| cetyl alcohol | | 16.80 |
| glycerol monostearate NSE[8] | | 2.85 |
| phospholipid EFA[9] | | 0.85 |
| tetrasodium EDTA | | 0.46 |
| silica, highly disperse, pyrogenic | | 0.11 |
| p-toluylenediamine | | 0.1 |
| 2,4,5,6-tetraaminopyrimidine | | 1.5 |
| 2-methyl resorcinol | | 0.8 |
| 2-amino-3-hydroxypyridine | | 0.05 |
| HC Red BN | | 0.8 |
| HC Red 3 | | 0.1 |
| methoxybutanol | | 1.43 |
| ammonia, 25% in water | to pH | 10.0 |
| ascorbic acid | | 0.1 |
| cetyl trimethyl ammonium bromide | | 0.5 |
| perfume | | 0.43 |
| water | to | 100 |

[1]hydroxyethyl cellulose (Hercules)
[2]bis(cocoyl)ethyl hydroxyethyl methyl ammonium methosulfate (INCI name: Dicocoylethyl Hydroxyethylmonium Methosulfate, Propylene Glycol; Henkel)
[3]solution of an ammonium salt of a methacrylic acid/methacrylate copolymer (INCI name: Ammonium Polyacrylate) (Röhm GmbH)
[4]solution of an ammonium salt of an acrylic acid polymer (INCI name: Ammonium Acrylates Copolymer) (Goodrich)
[5]oleyl alcohol + 7 EO units (Henkel)
[6]$C_{8-16}$-alkyl-1,4-polyglucoside (ca. 51% active substance; INCI name: Decyl Glucoside) (Henkel)
[7]oleic acid decyl ester (INCI name: Decyl Oleate) (Henkel)
[8](INCI name: Glyceryl Stearate) (Oleofina)
[9]ca. 30% active substance; INCI name: Linoleamidopropyl PG Dimonium Chloride Phosphate (Mona)

Example 2

In a volunteer with medium blond hair with very porous tips, the hair was divided by a center parting into a left-hand half and a right-hand half.

The left-hand half was treated as follows:

The porous tips were sprayed with ca. 10 g of formulation A2. After a contact time of 7 minutes at 25° C., the hair was treated over its entire length with a mixture of 30 g of formulation B2 and 30 g of a 6% aqueous hydrogen peroxide solution. After a contact time of 30 minutes at 25° C., the hair was rinsed with water, shampooed and blow-dried.

The right-hand half was treated as follows:

The hair was treated over its entire length with a mixture of 30 g of formulation B2 and 30 g of a 6% aqueous hydrogen peroxide solution. After a contact time of 30 minutes at 25° C., the hair was rinsed with water, shampooed and blow-dried.

Result:

The left-hand side was uniformly and intensively copper in color from the roots to the tips. The right-hand side was less uniformly and less intensively copper-colored.

Permanence Test:

The hair was washed daily on both sides for 12 days with a commercially available shampoo. The result showed that color removal is greater on the right-hand side than on the left-hand side.

| Formulation A2 | | |
|---|---|---|
| Natrosol ® 250 HR | | 0.2 |
| Dehyquart ® L-80 | | 0.3 |
| panthenol | | 0.1 |
| p-hydroxybenzoic acid methyl ester | | 0.03 |
| p-hydroxybenzoic acid propyl ester | | 0.03 |
| methoxybutanol | | 2.0 |
| 3-nitro-4-aminophenol | | 0.2 |
| water | to | 100 |
| Formulation B2 | | |
| ammonium carbopol solution, 1% in water | | 17.25 |
| ammonium rohagit solution, 6% in water | | 5.25 |
| Oleth-7 | | 5.70 |
| potassium olein soap, 12.5% in water | | 3.45 |
| Plantaren ® 2000 | | 0.53 |
| titanium dioxide anatase, type AS 05 | | 0.48 |
| Cetiol ® V | | 3.45 |
| cetyl alcohol | | 16.80 |
| glycerol monostearate NSE | | 2.85 |
| phospholipid EFA | | 0.85 |
| tetrasodium EDTA | | 0.46 |
| silica, highly disperse, pyrogenic | | 0.11 |
| p-toluylenediamine | | 0.4 |
| 2-amino-3-hydroxypyridine | | 0.1 |
| 3-methyl-4-aminophenol | | 0.3 |
| resorcinol | | 0.06 |
| 2-methylresorinol | | 0.04 |
| 2-hydroxy-4-aminotoluene | | 0.2 |
| methoxybutanol | | 1.43 |
| ammonia, 25% in water | to pH | 10.0 |
| ascorbic acid | | 0.1 |
| cetyl trimethyl ammonium bromide | | 0.5 |
| perfume | | 0.43 |
| water | to | 100 |

Example 3

In a volunteer with light blond hair with very porous tips, the hair was divided by a center parting into a left-hand half and a right-hand half.

The left-hand half was treated as follows:

The porous tips were sprayed with ca. 7 g of formulation A3. After a contact time of 5 minutes, the hair was treated over its entire length with a mixture of 30 g of formulation B3 and 30 g of a 6% aqueous hydrogen peroxide solution. After a contact time of 30 minutes at 25° C., the hair was rinsed with water, shampooed and blow-dried.

The right-hand half was treated as follows:

The hair was treated over its entire length with a mixture of 30 g of formulation B3 and 30 g of a 6% aqueous hydrogen peroxide solution. After a contact time of 30 minutes at 25° C., the hair was rinsed with water, shampooed and blow-dried.

Result:

The left-hand side was uniformly and intensively gold in color from the roots to the tips. The right-hand side was less uniformly and less intensively gold-colored.

Permanence Test:

The hair was washed daily on both sides for 12 days with a commercially available shampoo. The result showed that color removal is greater on the right-hand side than on the left-hand side.

| Formulation A3 | | |
|---|---|---|
| Natrosol ® 250 HR | | 0.2 |
| Dehyquart ® L-80 | | 0.3 |
| panthenol | | 0.1 |
| p-hydroxybenzoic acid methyl ester | | 0.03 |
| p-hydroxybenzoic acid propyl ester | | 0.03 |
| methoxybutanol | | 2.0 |
| HC Red 3 | | 0.1 |
| HC Yellow No. 2 | | 0.2 |
| water | to | 100 |
| Formulation B3 | | |
| ammonium carbopol solution, 1% in water | | 17.25 |
| ammonium rohagit solution, 6% in water | | 5.25 |
| Oleth-7 | | 5.70 |
| potassium olein soap, 12.5% in water | | 3.45 |
| Plantaren ® 2000 | | 0.53 |
| titanium dioxide anatase, type AS 05 | | 0.48 |
| Cetiol ® V | | 3.45 |
| cetyl alcohol | | 16.80 |
| glycerol monostearate NSE | | 2.85 |
| phospholipid EFA | | 0.85 |
| tetrasodium EDTA | | 0.46 |
| silica, highly disperse, pyrogenic | | 0.11 |
| p-toluylenediamine | | 0.5 |
| 2-methylresorcinol | | 0.2 |
| resorcinol | | 0.05 |
| 2-amino-3-hydroxypyridine | | 0.05 |
| m-aminophenol | | 0.02 |
| 4-chlororesorcinol | | 0.05 |
| methoxybutanol | | 1.43 |
| ammonia, 25% in water | to pH | 10.0 |
| ascorbic acid | | 0.1 |
| cetyl trimethyl ammonium bromide | | 0.5 |
| perfume | | 0.43 |
| water | to | 100 |

What is claimed is:

1. A process for coloring keratin fibers comprising:
   (a) applying a pretreatment composition onto keratin fibers, wherein the pretreatment composition comprises at least one substantive dye and at least one fiber-structure-improving agent selected from the group consisting of panthenol, one or more physiologically compatible panthenol derivatives, one or more plant extracts, honey extracts and combinations thereof; and
   (b) applying to the keratin fibers a coloring composition comprising at least one oxidation dye precursor or synthetic substantive dye or combinations thereof, after applying the pretreatment composition.

2. The process of claim 1, wherein the pretreatment composition is applied to the keratin fibers by spraying.

3. The process of claim 1 wherein the substantive dye of the pretreatment composition is selected from one or more nitrobenzene derivatives, basic substantive dyes or triphenylmethane derivatives, or combinations thereof.

4. The process of claim 3 wherein the substantive dye is selected from 3-nito-4-aminophenol, 4-(3'-hydroxyropylamino)-3-nitrophenol, 1,4(bis-(β-hydroxyethyl)-amino-2-nitrobenzene, 1-(β-hydroxyethylamino)-2-nitro-4-aminobenzene, 1-(β-hydroxyethylamino)-2-nitrobenzene, 4-(β-hydroxyethylamino)-3-nitrophenol, HC Blue 2, Basic Blue 99, Basic Red 76, Basic Brown 16 or Basic Brown 17, or combinations thereof.

5. The process of claim 4 wherein the substantive dye is present in the pretreatment composition in an amount of 0.001 weight percent to 20 weight percent, based on the total weight of the pretreatment composition.

6. The process of claim 5 wherein the substantive dye is present in the pretreatment composition in an amount of 0.005 weight percent to 5 weight percent, based on the total weight of the pretreatment composition.

7. The process of claim 1 wherein the pretreatment composition is contacted with the keratin fibers for 1 to 30 minutes before applying the coloring composition.

8. The process of claim 7 wherein the pretreatment composition is contacted with the keratin fibers for 1 to 10 minutes before applying the coloring composition.

9. The process of claim 1 wherein the pretreatment composition has a pH in the range from 3 to 9.

10. The process of claim 9 wherein the pretreatment composition has a pH in the range from 4 to 8.

11. The process of claim 1 wherein the oxidative dye precursor comprises at least one primary intermediate selected from p-phenylenediamine, p-toluylenediamine, p-aminophenol, 1-(2'-hydroxyethyl)-2,5-diaminobenzene, 4-amino-3-methylphenol, 2-aminomethyl-4-aminophenol or 2,4,5,6-tetraaminopyrimidine, or combinations thereof.

12. The process of claim 11 wherein the oxidative dye precursor further comprises at least one secondary intermediate selected from 2-chloro-6-methyl-3-aminophenol, 5-amino-2-methylphenol, 2-amino-3-hydroxypyridine, 2,6-di-(β-hydroxyethylamino)-toluene, 2-methyl resorcinol or 1-naphthol, or combinations thereof.

13. The process of claim 1 wherein the oxidative dye precursor comprises at least one secondary intermediate selected from 2-chloro-6-methyl-3-aminophenol, 5-amino-2-methylphenol, 2-amino-3-hydroxypyridine, 2,6-di-(β-hydroxyethylamino)-toluene, 2-methyl resorcinol or 1-naphthol, or combinations thereof.

14. The process of claim 1 wherein the oxidative dye precursor is oxidized with an oxidizing agent comprising hydrogen peroxide.

15. The process of claim 1 wherein the oxidative dye precursor is oxidized with an oxidizing system comprising one or more enzymes.

16. A process for coloring hair comprising applying to hair a pretreatment composition comprising at least one substantive dye and at least one fiber-structure-improving agent selected from the group consisting of panthenol, one or more physiologically compatible panthenol derivatives, one or more plant extracts, honey extracts and combinations thereof, and subsequently applying a coloring composition to obtain a uniform color over the length of the hair.

17. The process of claim 16 wherein the pretreatment composition is applied to the hair by spraying the pretreatment composition onto the hair.

18. The process of claim 16 wherein the pretreatment composition is applied to only the end portion of the hair.

* * * * *